United States Patent
Kudlik et al.

(10) Patent No.: US 11,786,721 B2
(45) Date of Patent: Oct. 17, 2023

(54) SLEEP MODE AND DO-NOT-DISTURB MODE FOR A LEFT VENTRICULAR ASSIST DEVICE

(71) Applicant: Medtronic, Inc., Minneapolis, MN (US)

(72) Inventors: D'Anne E. Kudlik, Saint Louis Park, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 347 days.

(21) Appl. No.: 17/141,558

(22) Filed: Jan. 5, 2021

(65) Prior Publication Data

US 2022/0211995 A1 Jul. 7, 2022

(51) Int. Cl.
*A61B 5/021* (2006.01)
*A61M 60/546* (2021.01)
(Continued)

(52) U.S. Cl.
CPC ............ *A61M 60/546* (2021.01); *A61B 5/021* (2013.01); *A61B 5/364* (2021.01); *A61M 60/178* (2021.01); *A61M 60/216* (2021.01); *A61M 2205/18* (2013.01); *A61M 2205/3365* (2013.01); *A61M 2205/3523* (2013.01);
(Continued)

(58) Field of Classification Search
CPC .......... A61B 2505/07; A61B 2560/028; A61B 2562/0247; A61B 5/02055; A61B 5/021; A61B 5/0245; A61B 5/0816; A61B 5/1116; A61B 5/1118; A61B 5/361; A61B 5/363; A61B 5/364; A61B 5/4836; A61B 5/686; A61B 5/7282; A61B 5/746; A61M 2205/18; A61M 2205/3334; A61M 2205/3365; A61M 2205/3523; A61M 2205/502; A61M 2205/52; A61M 2205/581; A61M 2205/582; A61M 2205/583; A61M 2230/62; A61M 2230/63; A61M 60/178; A61M 60/216; A61M 60/242; A61M 60/546
See application file for complete search history.

(56) References Cited

U.S. PATENT DOCUMENTS

7,997,854 B2    8/2011    LaRose et al.
8,007,254 B2    8/2011    LaRose et al.
(Continued)

*Primary Examiner* — George Manuel
(74) *Attorney, Agent, or Firm* — Shumaker & Sieffert, P.A.

(57) ABSTRACT

A controller for an implantable blood pump, having processing circuitry configured to control an operating speed of an impeller of the implantable blood pump. The processing circuitry being further configured to control activation and deactivation of a sleep mode. During the sleep mode the processing circuitry being configured to measure a level of suction by detecting suction during a predetermined time interval, recording the time at which suction occurred during the predetermined time interval, and generating a graph demonstrating the measured level of suction. The measured level of suction being a percentage of time the implantable blood pump experienced suction during the predetermined time interval. The processing circuitry being configured to reduce the operating speed of the impeller if the measured level of suction exceeds a predetermined threshold.

20 Claims, 5 Drawing Sheets

(51) Int. Cl.
   *A61M 60/178*   (2021.01)
   *A61M 60/216*   (2021.01)
   *A61B 5/364*    (2021.01)

(52) U.S. Cl.
   CPC ...  *A61M 2205/502* (2013.01); *A61M 2205/52* (2013.01); *A61M 2205/581* (2013.01); *A61M 2205/582* (2013.01); *A61M 2205/583* (2013.01)

(56) References Cited

U.S. PATENT DOCUMENTS

| | | |
|---|---|---|
| 8,419,609 B2 | 4/2013 | Shambaugh, Jr. et al. |
| 8,512,013 B2 | 8/2013 | LaRose et al. |
| 9,492,601 B2 | 11/2016 | Casas et al. |
| 9,561,313 B2 | 2/2017 | Taskin |
| 9,623,161 B2 | 4/2017 | Medvedev et al. |
| 2014/0275727 A1 | 9/2014 | Bonde et al. |
| 2016/0151553 A1* | 6/2016 | Bonde ................ A61M 60/873 455/411 |
| 2018/0028738 A1 | 2/2018 | Brown et al. |
| 2021/0260263 A1 | 8/2021 | Kudlik et al. |

* cited by examiner

SLEEP MODE AND DO-NOT-DISTURB MODE FOR A LEFT VENTRICULAR ASSIST DEVICE

CROSS-REFERENCE TO RELATED APPLICATION n/a.

FIELD

The present technology is generally related to implantable blood pump systems.

BACKGROUND

Implantable blood pumps, such as Ventricular Assist Devices (VAD), generally operate at a single programmed speed. Selection of the programmed speed is a difficult trade-off for many practitioners. Setting the speed of the pump too low can result in congestion, inability to exercise, and general heart failure symptoms. Conversely, setting the speed of the pump too high can result in suction, hypertension, hemolysis, stroke, right heart failure, and arrhythmias. The high variability of patient activity throughout the day, from sleep to exertion, compounds the difficulty of finding a single speed that minimizes the adverse events.

Left Ventricular Assist Devices (LVAD) produce a variety of alerts to warn the patient of concerning situations. Some alerts may warn of depletion of the pump battery or pump malfunction, while other alerts may warn of the detection of suction or low pulsatility. The alerts are typically very disruptive, making sleep more difficult and risking public embarrassment for the patient.

SUMMARY

The techniques of this disclosure generally relate to systems and methods for controlling the operating speed of an implantable blood pump.

In one aspect, the present disclosure provides a controller for an implantable blood pump. The controller including processing circuitry configured to control an operating speed of an impeller of the implantable blood pump. The processing circuitry being further configured to control activation and deactivation of a sleep mode. During the sleep mode the processing circuitry being configured to measure a level of suction by detecting suction during a predetermined time interval, recording the time at which suction occurred during the predetermined time interval, and generating a histogram demonstrating the measured level of suction. The measured level of suction being a percentage of time the implantable blood pump experienced suction during the predetermined time interval. The processing circuitry being configured to reduce the operating speed of the impeller if the measured level of suction exceeds a predetermined threshold.

In another aspect, the processing circuitry is further configured to perform a preliminary reduction of the operating speed of the impeller upon activation of the sleep mode.

In another aspect, if the measured level of suction exceeds a predetermined threshold, the controller is configured to generate a recommendation to a clinician for adjusting the operating speed of the impeller.

In another aspect, the processing circuitry is configured to generate and transmit an alert signal to at least one selected from the group consisting of an external controller, a mobile device, a tablet, and a smart device when measured level of suction exceeds the predetermined threshold.

In another aspect, the alert signal is one selected from the group consisting of a low urgency alert and a high urgency alert.

In another aspect, the low urgency alert and the high urgency alert are each at least one selected from the group consisting of an audible alert notification, a visual alert notification, and a tactile alert notification.

In another aspect, the at least one selected from the group consisting of the external controller, the mobile device, the tablet, and the smart device is configured to silence the low urgency alert during the sleep mode.

In another aspect, the processing circuitry is further configured to adjust the operating speed of the impeller based on at least one selected from the group consisting of body activity, body movement, and body position.

In another aspect, the sleep mode is activated via the at least one selected from the group consisting of the external controller, the mobile device, the tablet, and the smart device.

In another aspect, the processing circuitry is also configured to measure a level of at least one selected from the group consisting of hypertension, hypotension, hemolysis, stroke, heart failure, arrhythmias, and pump failure.

In another aspect, a method of controlling an operating speed of an impeller disposed within an implantable blood pump. The method comprising activating a sleep mode and measuring a level of suction within the implantable blood pump by detecting suction during a predetermined time interval, recording the time at which suction occurred during the predetermined time interval, and generating a graph demonstrating the measured level of suction. The measured level of suction being a percentage of time the implantable blood pump experienced suction during the predetermined time interval. The method further comprising decreasing the operating speed of the impeller if the measured level of suction exceeds a predetermined threshold.

In another aspect, the sleep mode is activated at a preset time.

In another aspect, the operating speed of the impeller preliminarily reduced upon activation of the sleep mode.

In another aspect, the method further including generating a recommendation for adjusting the operating speed of the impeller based on the measured level of suction, the recommendation being transmitted to a clinician.

In another aspect, the method further including generating at least one selected from the group consisting of a low urgency alert and a high urgency alert if the measured level of suction exceeds the predetermined threshold.

In another aspect, the low urgency alert and the high urgency alert are each at least one selected from the group consisting of an audible alert notification, a visual alert notification, and a tactile alert notification In another aspect, the method further including transmitting the at least one selected from the group consisting of the low urgency alert and the high urgency alert to at least one selected from the group consisting of an external controller, a mobile device, a tablet, and a smart device.

In another aspect, the low urgency alert is silenced via the at least one selected from the group consisting of the external controller, the mobile device, the tablet, and the smart device.

In yet another aspect, the disclosure provides an implantable blood pump system having a sleep mode. The implantable blood pump system including an internal controller having processing circuitry configured to control an operating speed of an impeller of an implantable blood pump, and activate and deactivate the sleep mode. The sleep mode being activated at a first preset time and deactivated at a second preset time. The operating speed of the impeller being preliminarily reduced upon activation of the sleep mode. The processing circuitry being further configured to measure a level of suction. When the sleep mode is activated, the level of suction of the implantable blood pump being measured by detecting suction during a predetermined time interval, recording the time at which suction occurred during the predetermined time interval, and generating a graph demonstrating the measured level of suction. The measured level of suction being a percentage of time the implantable blood pump experienced suction during the predetermined time interval. The processing circuitry being further configured to further reduce the operating speed of the impeller if the measured level of suction exceeds a predetermined threshold and generate at least one selected from the group consisting of a low urgency alert and a high urgency alert when the measured level of suction exceeds the predetermined threshold. The low urgency alert being silenced when the sleep mode is activated. The processing circuitry being further configured to transmit the at least one selected from the group consisting of the low urgency alert and the high urgency alert to at least one selected from the group consisting of an external controller, a mobile device, a tablet, and a smart watch when the measured level of suction exceeds the predetermined threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
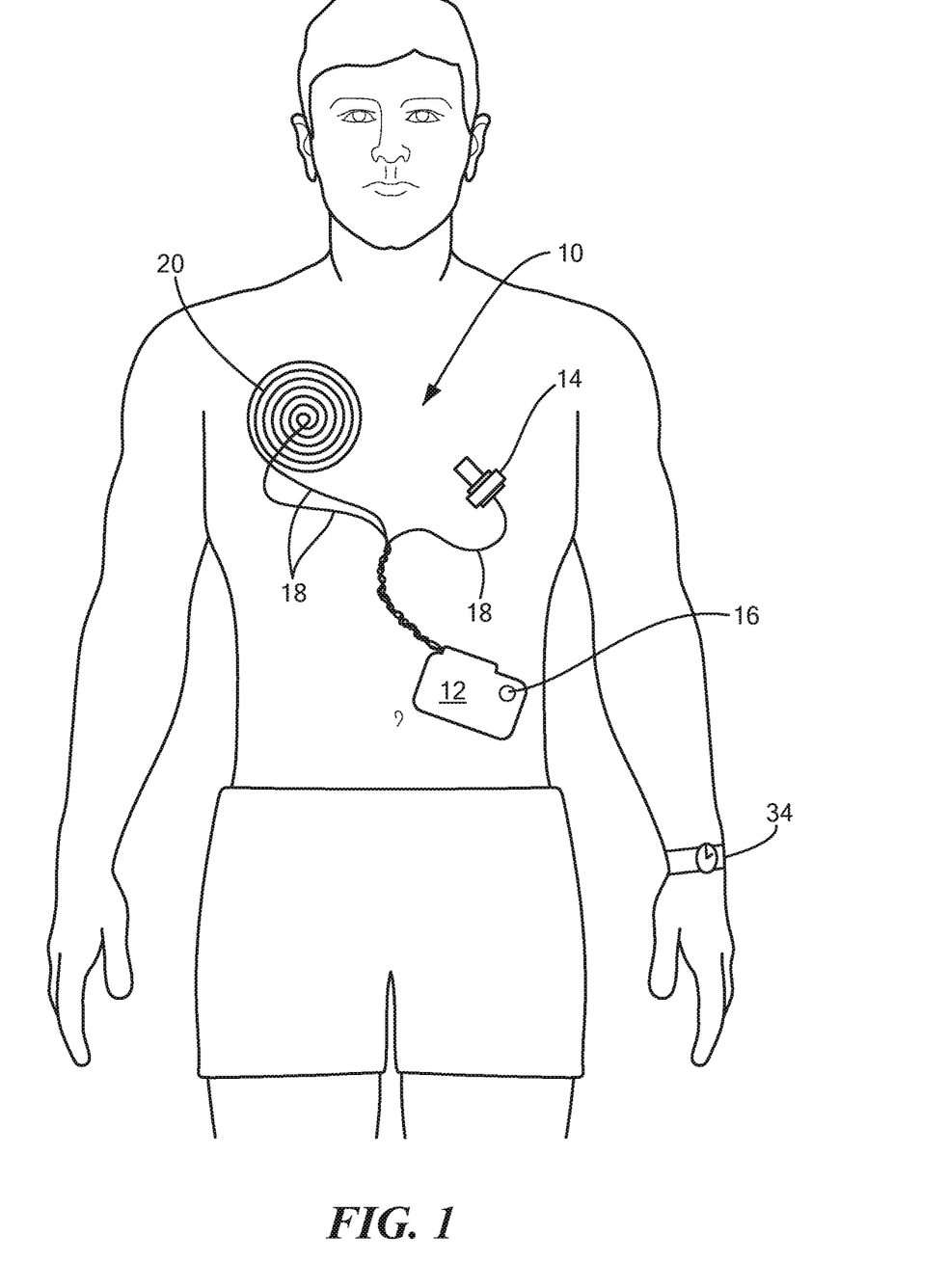
FIG. 1 is an internal system view of an implantable blood pump with a TETS receiver source constructed in accordance with the principles of the present application.
Figure 2:
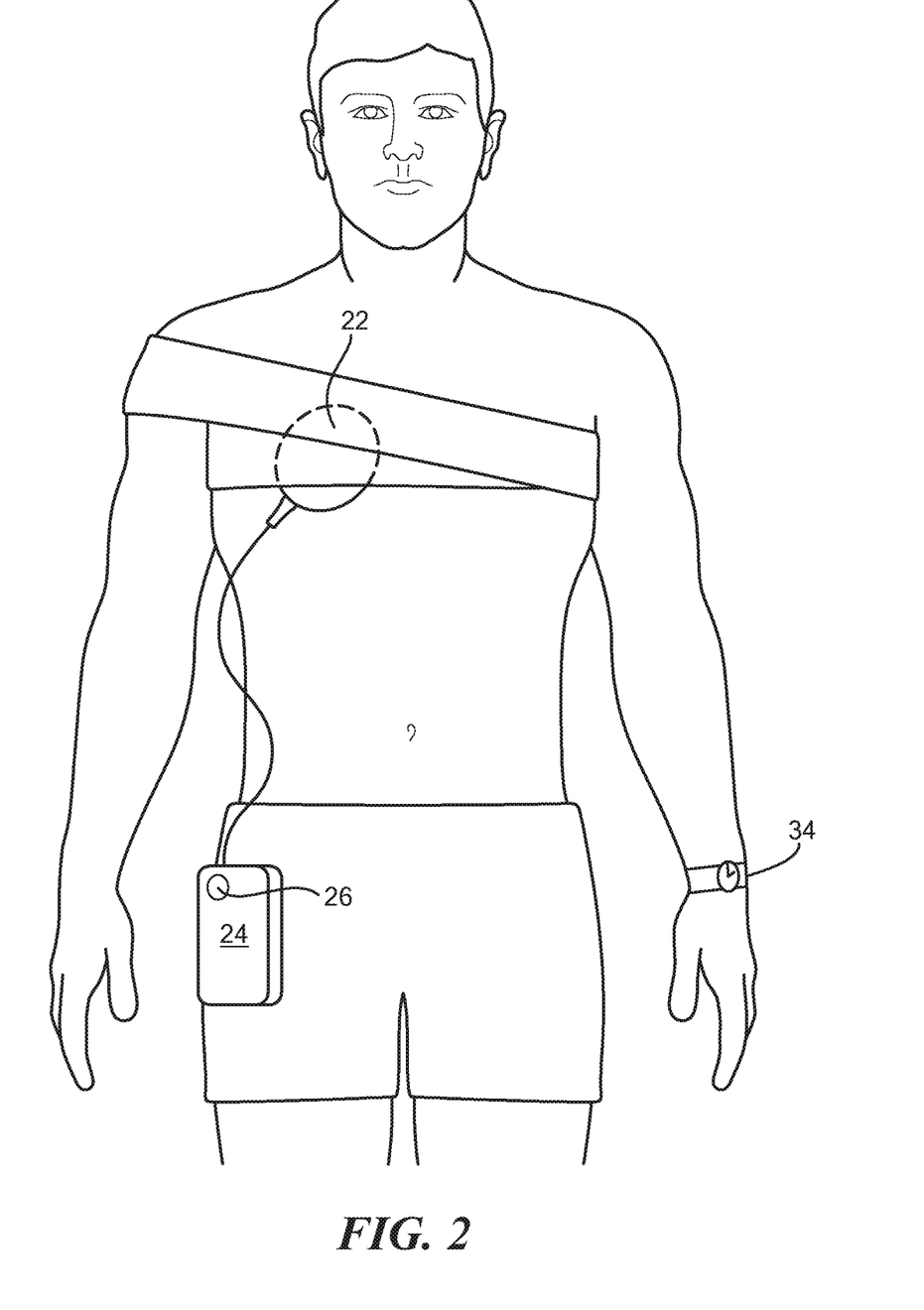
FIG. 2 is an external view of a TETS transmitter, and a controller of the system shown in FIG. 1.

Referring now to the drawings in which like reference designators refer to like elements there is shown in FIGS. 1 and 2 an exemplary mechanical circulatory support device ("MCSD") constructed in accordance with the principles of the present application and designated generally as "10." The MCSD 10 may be fully implantable within a patient, whether human or animal, which is to say there are no percutaneous connections between the implanted components of the MCSD 10 and the components outside of the body of the patient. In the configuration shown in FIG. 1, the MCSD 10 includes an internal controller 12 implanted within the body of the patient. The internal controller 12 includes a control circuit 13 having a processor 15 having processing circuitry configured to control operation of an implantable blood pump 14. The internal controller 12 may include an internal power source, configured to power the components of the controller 12 and provide power to one or more implantable medical devices, for example, the implantable blood pump, such as a ventricular assist device ("VAD") implanted within the left ventricle of the patient's heart. The power source may include a variety of different types of power sources including an implantable battery 16. VADs may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the blood pump 14 is electrically coupled to the internal controller 12 by one or more implanted conductors 18 configured to provide power to the pump 14, relay one or more measured feedback signals from the pump 14, and/or provide operating instructions to the pump 14.

Continuing to refer to FIGS. 1 and 2, a receiving or internal coil 20 may also be coupled to the internal controller 12 by, for example, the one or more implanted conductors and/or cables 18. In an exemplary configuration, the receiving coil 20 may be implanted subcutaneously proximate the thoracic cavity, although any subcutaneous position may be utilized for implanting the receiving coil 20. The receiving coil 20 is configured to be inductively powered through the patient's skin by a transmission or external coil 22 (seen in FIG. 2) disposed opposite the receiving coil 20 on the outside/exterior of the patient's body. For example, as shown in FIG. 2, a transmission coil 22 may be coupled to an external controller 24 having a power source, for example, a portable battery 26 carried by the patient or wall power. In one configuration, the battery 26 is configured to generate a radiofrequency signal for transmission of energy from the transmission coil 22 to the receiving coil 20. The receiving coil 20 may be configured for transcutaneous inductive communication with the transmission coil 22 to define a transcutaneous energy transfer system (TETS) that receives power from the transmission coil 22. Further, the controller 12 described herein may also be used with partially implantable VAD systems. In such systems, the controller 12 described herein may be used as a similarly configured external controller with percutaneous connections to the blood pump 14.

Figure 3:
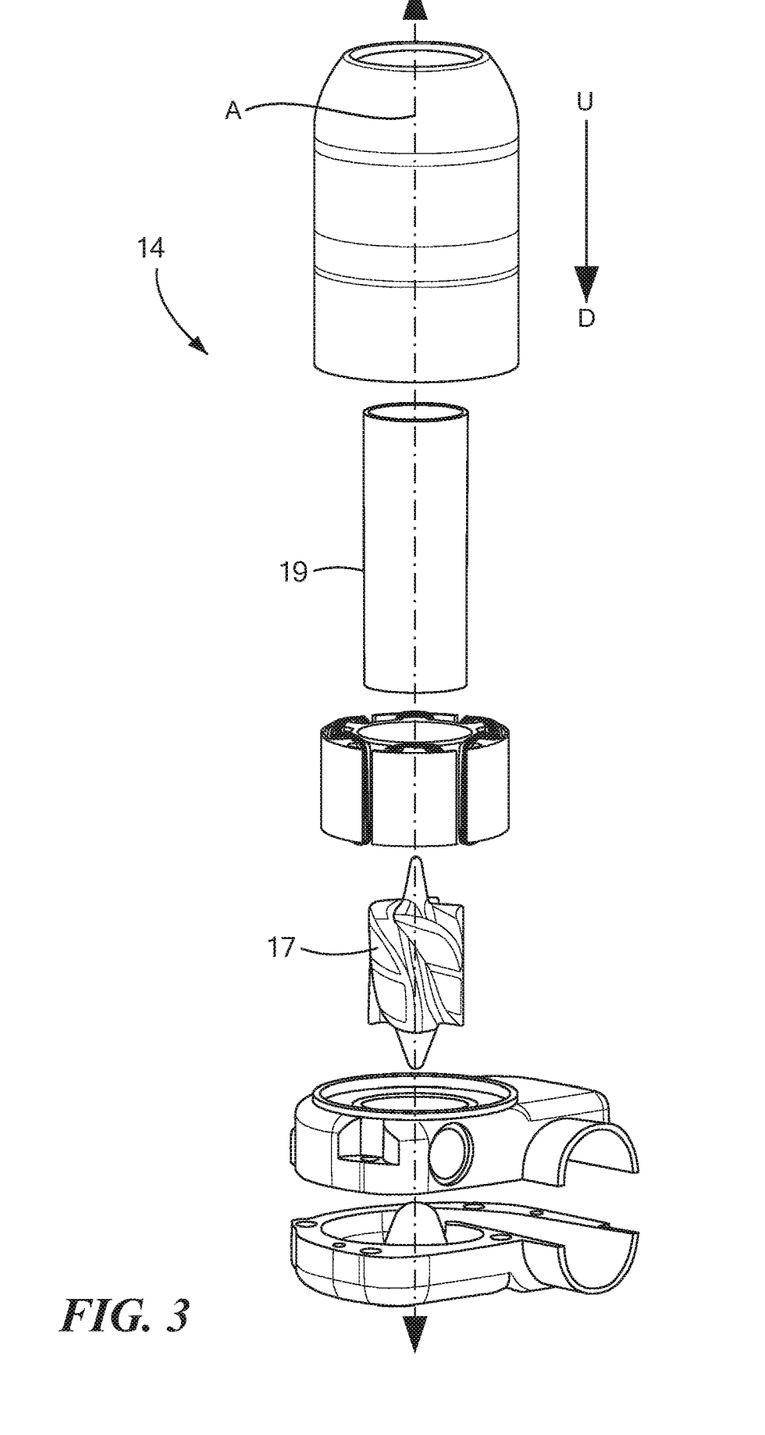
FIG. 3 is a disassembled view of an exemplary blood pump constructed in accordance with the principles of the present application.

Referring now to FIG. 3, as mentioned above, the blood pump 14 may be, without limitation, the HVAD® pump or the MVAD® pump, having a movable element, such as an impeller 17 or a rotor, configured to rotate about axis "A" and impel blood form the heart to the rest of the body. The impeller 17 may rotate within a tube 19 extending from a proximal upstream end to a distal downstream end. The HVAD® Pump is further discussed in U.S. Pat. No. 8,512,013, the disclosure of which is incorporated herein by reference in the entirety. The MVAD® Pump is further discussed in U.S. Pat. Nos. 8,007,254 and 9,561,313, the disclosures of which are incorporated herein by reference in the entirety.

Figure 4:
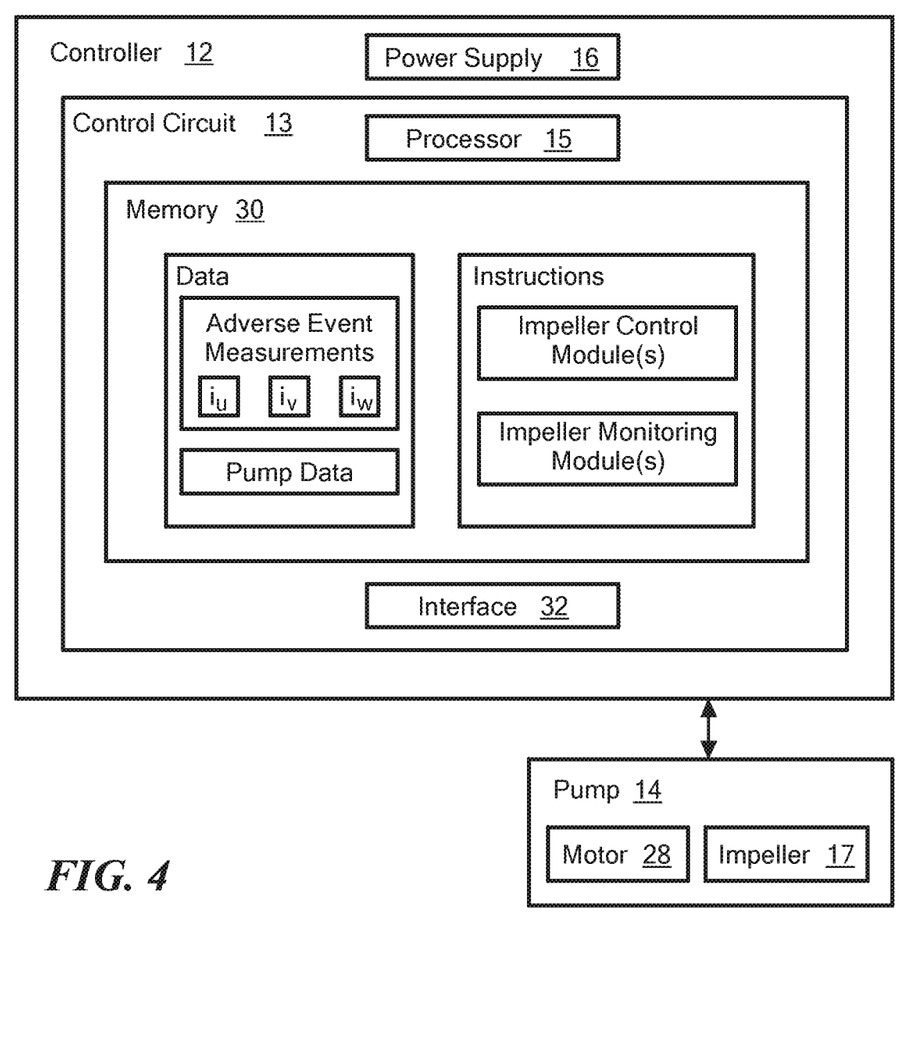
FIG. 4 is a block diagram showing a control system and pump of the present application.

FIG. 4 is a block diagram of an exemplary system for controlling a pump speed and/or other operations of the implantable blood pump 14 when the blood pump 14 is in communication with the system. The blood pump 14 includes a motor 28 therein and may be a separate component or form part of the system. The system includes the controller 12 having a control circuit 13 and a processor 15 having processing circuitry configured to perform the operations of the blood pump 14. The system may also include a memory 30 and an interface 32, the memory 30 being configured to store information accessible by the processor 15. Such instructions and/or data include that which is used to control the pump speed and activation/deactivation of the sleep mode.

Continuing to refer to FIGS. 1-4, the processing circuitry is configured to control the operating speed of the impeller 17 and the activation and/or deactivation of a sleep mode, which may be activated and/or deactivated at a predetermined time selected by a clinician and/or a patient. The sleep mode may also be manually activated at any time desired by the patient, clinician, and/or any other caregiver. Upon activation and deactivation of the sleep mode, the processing circuitry may perform preliminary adjustments of the operating speed of the impeller 17 such that the speed of the impeller 17 is reduced when activated and increased once deactivated. For example, when the sleep mode is activated, the operating speed of the impeller 17 may be decreased by a predetermined difference from typical operating speed (e.g., −100 RPM) or may be lowered to a pre-selected speed (e.g., 2400 RPM) determined by the clinician. Alternatively, although it has been described herein that upon activation of the sleep mode, the operating speed of the impeller 17 is reduced, the clinician or patient may also configure the processing circuitry to increase or maintain the current operating speed of the impeller 17 upon activation of the sleep mode.

Once sleep mode has been activated by the processing circuitry, the controller 12 receives signals from the blood pump 14 through the one or more conductors 18 which provide information to the controller 12 regarding the operating parameters of the pump 14 while the patient is sleeping. The processing circuitry is configured to periodically and/or continuously detect and record the occurrence of at least one adverse event such as suction, hypertension, hypotension, hemolysis, stroke, heart failure, arrhythmias, pump failure, and the like. In situations wherein suction is detected, suction may be the result of the operating speed of the impeller being too high, and thus may require the operating speed of the impeller 17 to be decreased. Suction events may be detected by, including but not limited to, the methods described in U.S. Pat. No. 9,492,601, U.S. Patent Publication Number 2018/0028738, and U.S. patent application Ser. No. 16/795,929, the entireties of which are expressly incorporated by reference herein.

Figure 5:
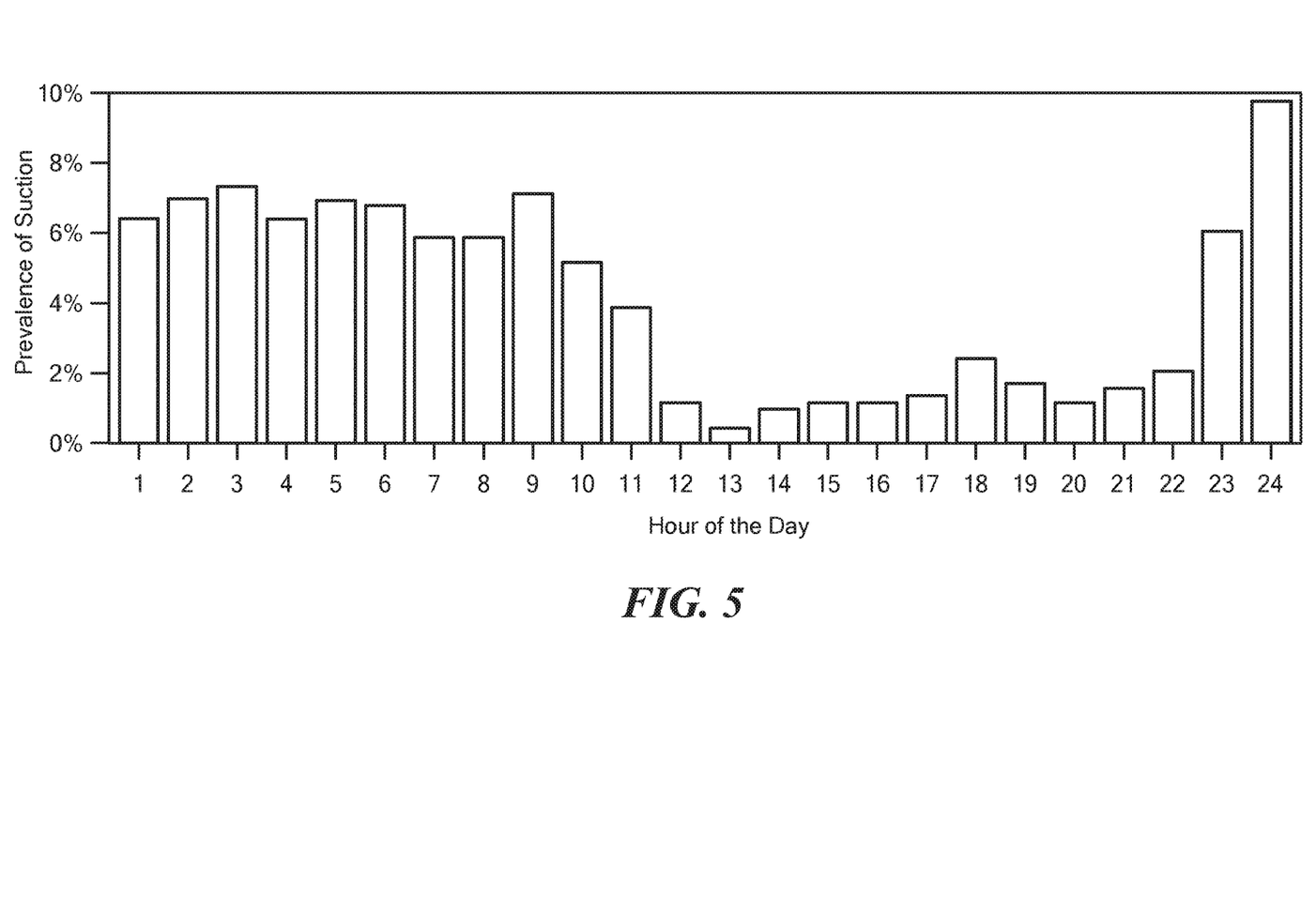
FIG. 5 is a generated graph illustrating the measured level of suction recorded by the blood pump of FIGS. 1-4.

The processing circuitry is configured to measure the level of suction by detecting suction during a predetermined time interval. The predetermined time interval may include 1-hour intervals of time between 9:00 pm and 7:00 am (the predetermined time interval is not restricted to 1-hour intervals and may instead be any period of time determined by the clinician and/or patient such as minutes, hours, days, weeks, months, or years). Once the sleep mode is activated at 9:00 pm, the processing circuitry is configured to detect suction. Once suction has been detected, the processing circuitry records how much suction was detected during each 1-hour interval and generates a histogram (as shown in FIG. 5), or other type of graph, demonstrating the measured level of suction. The measured level of suction is indicative of a percentage of time that the pump 14 experienced suction during each 1-hour time interval. Once the measured level of suction has been recorded and included in the graphical data, it is then compared against a predetermined threshold value set by a clinician or patient. If the processing circuitry determines that the measured level of suction exceeds the predetermined threshold, the operating speed of the impeller 17 may then be reduced by the processing circuitry.

The predetermined threshold may be any percentage of time the pump 14 experiences suction during a particular time interval, such as between the range of 0% of the time and 100% of the time. For example, as shown in the graph of FIG. 5, the processing circuitry records the percentage of time per each 1-hour interval that suction is detected in the pump 14. During hour 24 (11:00 pm-12:00 am) suction is detected for 10% of the 1-hour interval, meaning that the pump 14 experienced suction for 6 minutes during the 1-hour interval between 11:00 pm and 12:00 am. Additionally, the clinician may set any percentage of time in suction (e.g., 4%, 6%, 8%, 10%, 12%, etc.) as being the predetermined threshold. Thus, once the predetermined threshold is reached or surpassed, the processing circuitry may reduce the operating speed of the impeller 17 or generate a recommendation to the clinician or patient for reducing the operating speed.

Although the graph shown in FIG. 5 represents a 24-hour time interval, the graph may also display historical data obtained over an extended period such as, for example, any period of time within the last 7-days, 14-days, 21-days, 30-days, etc., and may influence the speed of the impeller 17 upon activation of the sleep mode on the current day. The influence of historical data obtained from prior days on the generated graph may be constant (i.e., each of the last 7-days or 14-days may be weighted equally) or could be exponentially decaying (i.e., the last night in the 7-days or 14-days has the highest weighting, the night immediately prior having less weighting, and the night prior to that having even less weighting). By analyzing the historical data, the controller 12 can determine what adjustments to the operating speed of the impeller 17 may be necessary, and may either perform these adjustments automatically or may generate and transmit a recommendation to the patient and/or clinician for whether the speed of the impeller 17 should be increased and/or decreased temporarily or permanently. As a further example of how the historical data may be used, if on a Monday and following Tuesday the operating speed of the impeller 17 is reduced at 10:00 pm, the processing circuitry may utilize learning behavior to automatically reduce the operating speed of the impeller 17 to the same reduced speed either before or at 10:00 pm on the following Wednesday or any other subsequent day.

Further, although it has been mentioned that the sleep mode may be activated from 9:00 pm-7:00 am, the controller 12 may activate the sleep mode at any other time of the day and/or night that is determined by a clinician or the patient in order to address each patient's particular sleep schedule. The sleep mode may also be patient initiated/scheduled via the external controller 24 or the sleep mode may be initiated/scheduled remotely by a clinician using another controller, monitor, tablet, computer, or smart device.

In addition to adjusting the operating speed of the impeller when the predetermined threshold has been reached or exceeded, the processing circuitry is also configured to generate and transmit a low urgency alert and/or a high urgency alert to at least one of the external controller 24, mobile device, tablet, smart watch 34, or the like (not shown). The low and high urgency alerts may each consist of audible, visual, and/or tactile alert notifications to warn the patient of the adverse event (e.g., suction detection). The external controller 24 or the patient's mobile device, tablet, or smart watch 34 may be configured to automatically silence the low urgency alerts so that the patient is not disturbed while they are sleeping. However, high urgency alerts will not be silenced and thus will be relayed to the patient indicating that immediate attention is required. The controller 12 will determine whether the occurrence of the at least one adverse event warrants a low or high urgency alert based on the type of adverse event and its effects on the operation of the blood pump 14.

Further, the controller 12 may be pre-configured by the patient or clinician to deactivate the sleep mode at a pre-scheduled time or after a predetermined duration of time, such as, for example, 5-10 hours. The patient may also deactivate the sleep mode at any point via the external controller 24, mobile device, tablet, or smart watch 34.

Although the sleep mode may be deactivated during the patient's waking hours, the processing circuitry may continue to detect and record the occurrences of any adverse event, such as suction, and is configured to generate additional graphical data that can be used to provide recommendations and suggestions to the clinician for adjusting the operating speed of the impeller during the patient's waking hours.

The processing circuitry may also be configured to monitor physiological readings of the patient, such as, for example, the following: heart rate, respiratory rate, tidal volume, EKG, body temperature, body position, body movement, etc., or any combinations thereof. By analyzing these physiological readings, the controller 12 may determine that an increase in patient activity has occurred and may automatically deactivate the sleep mode and resume normal "waking hour" operation. However, if any of these physiological readings exceed a predetermined threshold, the controller 12 may be configured to generate and transmit the low urgency alert and/or high urgency alert to the external controller 24. The processing circuitry may also record these physiological readings in a log that is provided to the clinician. The processing circuitry may also use these detected physiological readings to generate additional graphical data to provide recommendations and suggestions to the clinician for adjusting the operating speed of the impeller 17 during the patient's waking and/or sleep hours.

Further, the controller 12 and processing circuitry described herein are also configured to activate a "do-not-disturb" mode which is configured to cooperate with the described sleep mode. The do-not-disturb mode automatically silences low urgency alerts so that the user or patient is not disturbed by the alert. The user may manually activate the do-not-disturb mode when desired via the external controller 24, mobile device, tablet, or smart watch 34, or the user and/or clinician may configure the controller 12 to automatically activate the do-not-disturb mode at particular times each day. Clinicians may also be able to remotely schedule "do-not-disturb" times for the patient remotely via the clinicians own remote controller, mobile device, tablet, or other type of smart device. However, although low urgency alerts may routinely be silenced by the do-not-disturb mode, high urgency alerts would not be silenced and thus a user would be notified of the alert and must then deactivate the alert manually via the external controller 24, mobile device, tablet, or smart watch 34.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable blood pump, the controller comprising:
   memory; and
   processing circuitry coupled to the memory and configured to:
   control an operating speed of an impeller of the implantable blood pump;
   control activation and deactivation of a sleep mode of the implantable blood pump, wherein the processing circuitry is configured to set the operating speed to a first operating speed in response to the sleep mode being activated and set the operating speed to a second operating speed in response to the sleep mode being deactivated;
   determine a level of suction, wherein to determine the level of suction, the processing circuitry is further configured to:
   detect suction during a predetermined time interval while the sleep mode is activated;
   record one or more times at which suction occurred during the predetermined time interval; and
   determine the level of suction based on a percentage of time the implantable blood pump experienced suction during the predetermined time interval; and reduce, while the sleep mode is activated, the operating speed of the impeller from the first operating speed in response to the level of suction exceeding a predetermined threshold.

2. The controller of claim 1, wherein the processing circuitry is configured to perform a preliminary reduction of the operating speed of the impeller to the first operating speed in response to activation of the sleep mode.

3. The controller of claim 1, wherein the processing circuitry is configured to generate a recommendation to a clinician for adjusting the operating speed of the impeller in response to the level of suction exceeding the predetermined threshold.

4. The controller of claim 1, wherein the processing circuitry is configured to generate and transmit an alert signal to one or more of an external controller, a mobile device, a tablet, or a smart device in response to the level of suction exceeding the predetermined threshold.

5. The controller of claim 4, wherein the alert signal comprises one of a low urgency alert and or a high urgency alert.

6. The controller of claim 5, wherein the low urgency alert and the high urgency alert are each at least one consisting of an audible alert notification, a visual alert notification, or a tactile alert notification.

7. The controller of claim 1, wherein the processing circuitry is further configured to adjust the operating speed of the impeller based on at least one of body activity, body movement, or body position.

8. The controller of claim 1, wherein the processing circuitry is configured to measure a level of at least one of hypertension, hypotension, hemolysis, stroke, heart failure, arrhythmias, or pump failure.

9. The controller of claim 1, wherein to reduce the operating speed of the impeller from the first operating speed in response to the level of suction exceeding the predetermined threshold, the processing circuitry is configured to determine an amount to reduce the operating speed based on the level of suction.

10. The controller of claim 1, wherein the processing circuitry is further configured to activate the sleep mode at a preset time.

11. The controller of claim 1, wherein the processing circuitry is further configured to deactivate the sleep mode at a preset time.

12. The controller of claim 1, wherein the processing circuitry is configured to increase the operating speed of the impeller to the second operating speed upon deactivation of the sleep mode.

13. The controller of claim 1, wherein the processing circuitry is configured to:
record a plurality of levels of suction in the memory; and
change the first operating speed based on the plurality of levels of suction.

14. A method comprising:
controlling, by processing circuitry, an operating speed of an impeller of an implantable blood pump;
controlling, by the processing circuitry, activation and deactivation of a sleep mode of the implantable blood pump, wherein controlling activation and deactivation of the sleep mode comprises setting the operating speed to a first operating speed in response to the sleep mode being activated and setting the operating speed to a second operating speed in response to the sleep mode being deactivated;
determining a level of suction, wherein determining the level of suction comprises:
detecting suction during a predetermined time interval while the sleep mode is activated;
recording one or more times at which suction occurred during the predetermined time interval; and
determining the level of suction based on a percentage of time the implantable blood pump experienced suction during the predetermined time interval; and
reducing, by the processing circuitry and while the sleep mode is activated, the operating speed of the impeller from the first operating speed in response to the level of suction exceeding a predetermined threshold.

15. The method of claim 14, further comprising:
determining, by the processing circuitry, an amount to reduce the operating speed based on the level of suction; and
reducing, by the processing circuitry, the operating speed of the impeller from the first operating speed by the determined amount in response to the level of suction exceeding the predetermined threshold.

16. The method of claim 14, wherein controlling activation and deactivation of the sleep mode comprises activating the sleep mode at a preset time.

17. The method of claim 14, wherein controlling activation and deactivation of the sleep mode comprises deactivating the sleep mode at a preset time.

18. The method of claim 14, further comprising:
increasing, by the processing circuitry, the operating speed of the impeller to the second operating speed in response to deactivation of the sleep mode.

19. The method of claim 14, further comprising:
recording a plurality of levels of suction; and
changing the first operating speed based on the plurality of levels of suction.

20. The method of claim 14, further comprising:
generating a recommendation to a clinician for adjusting the operating speed of the impeller in response to the level of suction exceeding the predetermined threshold.

* * * * *